(12) United States Patent
Poisner

(10) Patent No.: US 8,727,208 B2
(45) Date of Patent: May 20, 2014

(54) METHOD FOR IDENTIFYING PILLS VIA AN OPTICAL DEVICE

(75) Inventor: David Poisner, Folsom, CA (US)

(73) Assignee: Intel-GE Care Innovations LLC, Roseville, CA (US)

( * ) Notice: Subject to any disclaimer, the term of this patent is extended or adjusted under 35 U.S.C. 154(b) by 1063 days.

(21) Appl. No.: 11/477,676

(22) Filed: Jun. 30, 2006

(65) Prior Publication Data

US 2008/0000979 A1    Jan. 3, 2008

(51) Int. Cl.
*G06F 19/00* (2011.01)
*G01N 21/95* (2006.01)
*G01N 21/35* (2014.01)
*A61J 3/07* (2006.01)
*A61J 3/00* (2006.01)
*G07F 17/00* (2006.01)

(52) U.S. Cl.
CPC .......... *G01N 21/9508* (2013.01); *G01N 21/359* (2013.01); *A61J 3/074* (2013.01); *A61J 3/007* (2013.01); *G07F 17/0092* (2013.01)
USPC ....... 235/375; 235/454; 235/462.01; 235/494

(58) Field of Classification Search
USPC ............ 73/865.8; 235/435, 439, 454, 462.01, 235/462.23, 462.24; 382/181, 182
See application file for complete search history.

(56) References Cited

U.S. PATENT DOCUMENTS

| | | | | |
|---|---|---|---|---|
| 792,918 A * | 6/1905 | Ohlendorf et al. ............ 222/170 |
| 3,756,402 A * | 9/1973 | Wagers et al. ................ 209/541 |
| 4,143,770 A * | 3/1979 | Grimmell et al. ............. 209/558 |
| 4,882,493 A * | 11/1989 | Lodder .......................... 250/353 |
| 5,372,276 A * | 12/1994 | Daneshvar ........................ 221/2 |
| 5,661,249 A * | 8/1997 | Rupp et al. ..................... 73/865.8 |
| 5,700,998 A * | 12/1997 | Palti ............................... 235/375 |
| 5,884,806 A * | 3/1999 | Boyer et al. ..................... 221/75 |
| 5,992,742 A * | 11/1999 | Sullivan et al. .......... 235/462.01 |
| 6,079,284 A * | 6/2000 | Yamamoto et al. ........... 73/865.8 |
| 6,260,419 B1 * | 7/2001 | Kramer ........................... 73/821 |
| 6,267,265 B1 * | 7/2001 | Issa ................................ 221/288 |
| 6,535,637 B1 * | 3/2003 | Wootton et al. ............... 382/190 |
| 6,543,692 B1 * | 4/2003 | Nellhaus et al. ......... 235/462.01 |
| 6,771,369 B2 * | 8/2004 | Rzasa et al. .................... 356/326 |
| 6,820,498 B2 * | 11/2004 | Kalbermatten ................. 73/856 |
| 7,006,214 B2 * | 2/2006 | Rzasa et al. .................... 356/300 |
| 7,042,231 B2 * | 5/2006 | Trebbi .......................... 324/639 |
| 7,059,526 B1 * | 6/2006 | Sullivan et al. .......... 235/462.01 |
| 7,218,395 B2 * | 5/2007 | Kaye et al. ..................... 356/301 |
| 7,364,103 B2 * | 4/2008 | Kraemer et al. .............. 241/262 |
| 7,398,279 B2 * | 7/2008 | Muno et al. .......................... 1/1 |
| 7,616,117 B2 * | 11/2009 | Streeb et al. ................. 340/572.1 |
| 2003/0189089 A1 * | 10/2003 | Raistrick et al. .............. 235/375 |
| 2005/0150805 A1 * | 7/2005 | Burchell ....................... 206/534 |
| 2005/0288906 A1 * | 12/2005 | Drennen et al. ............... 702/189 |
| 2006/0124656 A1 * | 6/2006 | Popovich, Jr. ..................... 221/9 |
| 2006/0263461 A1 * | 11/2006 | Mertens et al. ............... 425/135 |
| 2007/0246327 A1 * | 10/2007 | Stueckle .................... 198/345.1 |
| 2007/0265880 A1 * | 11/2007 | Bartfeld et al. .................... 705/2 |

\* cited by examiner

*Primary Examiner* — Christopher Stanford
(74) *Attorney, Agent, or Firm* — Pillsbury Winthrop Shaw Pittman LLP

(57) ABSTRACT

A pill identification device having a mechanical device that is adapted to roll a pill along various axes of the pill, an optical device to record or transmit images of the pill and an algorithm to compare an identifier of the pill to a database having known identifiers of known pills is disclosed. A method of identifying a pill using the pill identification device of the embodiment of this invention is disclosed herein. Also, a method of manufacturing the pill identification device of the embodiments of this invention is disclosed herein.

8 Claims, 3 Drawing Sheets

PRIOR ART

METHOD FOR IDENTIFYING PILLS VIA AN OPTICAL DEVICE

RELATED APPLICATIONS

None.

FIELD OF INVENTION

Embodiments of the invention relate to the field of identification of drug tablets, capsules, pills and the like (generically called a "pill" in this application). More particularly, the embodiments of the invention relate to a method and a system for identification of pills, the system being configured for secure and accurate identification of the pills, preferably by optical methods.

BACKGROUND

Patients are often admitted to emergency rooms or visit a new doctor, when the patient is in possession of medicine that is not in the original prescription container. For example, the patient may have removed the pills and put them in plastic bags.

In some cases there is a need to quickly identify the specific pills. For example, when a person is brought into a police station in possession of some pills and the police need to determine whether the pills are abusive narcotics or some other pills required for some ailment of the person. While all health care professionals, including paramedics or first responders, and law enforcement agencies have a critical role to play in minimizing the abuse and diversion of narcotics and controlled substances, they need better tools to identify pills, capsules, tablets, etc.

Currently, one of the methods of identifying an unknown pill is by chemical analysis of the pill. This procedure is expensive, time consuming and destructive as the pill is generally destroyed during the analysis, which may be an issue if the is pill needed for evidence in a trial.

Besides, there are organizations such as Pharmer.org (see http://www.pharmer.org/), a non-profit educational resource, that help identify and teach about medicines that are prescribed. Such organizations have assembled some pill identification reference tools, which include data on imprints, and shape and color of the pills. For example, a common opioid painkiller medicine called Vicodin (shown in FIG. 1), within the family called hydrocodone/acetaminophen medicines, has the following pill identifiers: Manufacturer: Abbott Laboratories; Imprint/Markings: VICODIN: Strength (mg) hydrocodone/acetaminophen: 5/500; Color: White; Shape: Oblong; Brand: VICODIN; Comments: Scored. Other identifiers include size and codes, including a bar code. Unfortunately, many pills do not contain the name of the product as in the case of VICODIN. In addition, there is no automated system that allows detection of the identification reference parameters such as imprint, color, shape, etc.

Drug abusers may be difficult to distinguish from legitimate patients. The patient at a clinic or office claiming to have a migraine headache or back pain may be a legitimate sufferer. On the other hand, the individual may be seeking a controlled substance to feed an addiction, or a criminal looking for controlled substances to sell. To take a balanced approach to the prevention of drug abuse and diversion, health professionals must be able to accurately and rapidly identify pills carried by someone. Thus, there is a need for a rapid, accurate and automated pill identification system for health professionals who are authorized to prescribe narcotics and controlled substances, those who are authorized to dispense (e.g., pharmacists), those involved in administering these drugs (e.g., nurses), as well as all those involved in controlling trafficking of drugs (e.g., police). Such a pill identification system would allow health care providers and regulators to promote appropriate use of narcotics and controlled substances while at the same time minimizing their abuse and diversion.

The embodiments of the invention relate to a rapid, accurate and automated pill identification system. The embodiments of the invention would strengthen the rational for prescription use of narcotics and other controlled substances and minimize their abuse and diversion through easy and accurate identification of pills.

DETAILED DESCRIPTION

Figure 1:
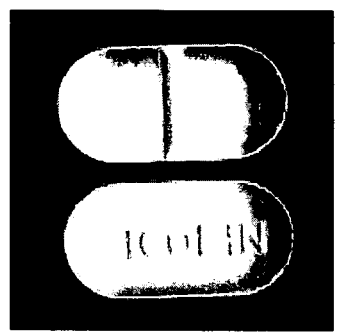
FIG. 1 shows a pill of VICODIN.

The term "pill" refers to a pill, a tablet, a capsule, or any other solid form used for delivering a drug into the body of a living creature.

The embodiments of the invention include a pill identification device, system, and method of using the same. The embodiments of invention address the need for flexible, inexpensive and independent identification of a pill via a self-contained and independent pill identification device (an apparatus for identification of a pill) that has the ability to process the images of the pill locally and then transmit a processed signal to one or more central collection points or base stations that could integrate multiple images and identify the pill. In other embodiments of the invention, the images may not be processed locally, but transmitted to the base station that processes the images and integrates multiple images and identifies the pill. The embodiments of the invention include a pill identification device that could wirelessly transmit and receive a signal and associated infrastructure. The base station could also be informed of the geographic location of the pill identification device through the use of GPS technology built into the pill identification device. The pill identification device could further provide two-way communication between the pill identification device and the base station, enhancing monitoring of decisions made and reducing human error.

In some embodiments of the invention, the pill identification device could transmit and receive a signal to the base station by both wireless and hard-wired connections such as Ethernet. The wireless standard could be a 2.4 GHz WLAN or IEEE 802.11 Standard (802.11, 1999/8802-11 (International Organization for Standardization/International Electrotechnical Commission) (ISO/IEC) 8802-11:1999), for example. In further embodiments of the invention, multiple pill identification devices could be present on the same network.

Furthermore, the pill identification device could have an ability to determine the base station to send the processed signal from among a plurality of base stations. Preferably, the pill identification device could have the ability to hand off the processed signal from a first base station to a second base station as the pill identification device moves out of a communication range of the first base station. Also, if the person undertaking the identification of the pill, e.g., a police office, goes out of two-way communication range with a base station, the pill identification device could have an automatic reconnect and synchronization with the base station as the person returns within a two-way communication coverage range.

In another embodiment of the invention, the invention can include enhanced device mobility features. In some environments, both the pill identification device and the base station could be mobile. Thus, preferably, the communication network system could have a hand-off feature that would allow the pill identification device to adapt rapidly to changes in link quality from one base station to another base station. For example, if a multi-hop routing protocol is in use, it could find a new route and a new base station or router when a doctor moves from room to room during rounds.

In another embodiment of the invention, the invention can include multiple receivers, e.g., a police station, the Department of Motor Vehicles, a hospital, the Federal Bureau of Investigation, etc. The data from a given pill identification device could be received by multiple receivers. Thus, the communication network system should preferably support multicast semantics.

In another embodiment of the invention, communications can be made secure. A private-key and public-key cryptography scheme could be integrated into an appropriate authentication and authorization framework for the pill identification device network system.

In another embodiment of the invention, the pill identification device can include reliable communications. Although intermittent data packet loss due to interference may be acceptable, persistent data packet loss due to congestion or node mobility could degrade system performance. The image sampling rates may range anywhere from less than 1 Hz to 1000 Hz or more for wireless transmission of data related to the images of the pill to and from a wireless pill identification device.

The transmission from the pill identification device to the base station does not need to be done in real time, though it would be preferable for transmission to be done in real time. In some embodiments of the invention, it would be preferable for power consumption if the pill identification device transmitted data only when its microprocessor/algorithms indicated that there was a new image that needed to be transmitted. The pill identification device could also include a rechargeable battery such as an extended-life lithium ion battery.

In some embodiments of the invention, the pill identification device could include a display for convenient review and assessment of the pill. In addition, the pill identification device could have an emergency call button that could be pressed or activated by some other means for emergency help. The pill identification device could also have a distinctive signal mode (e.g., LED sets) that indicates that it is functioning normally, that the pill being identified is within normal parameters (such as size and shape of the pill) for identification by the pill identification device, and/or that the device is in acceptable contact with a wireless receiver.

In addition, the pill identification device of an embodiment of the invention could have self-diagnostic capabilities that would allow the pill identification device to know if it contains any leftover pill, a broken pill, or whether it is operating correctly. The pill identification device of the embodiments of the invention could also have other physical characteristics that make the pill identification device reusable, flexible and cost-effective.

Figure 2:
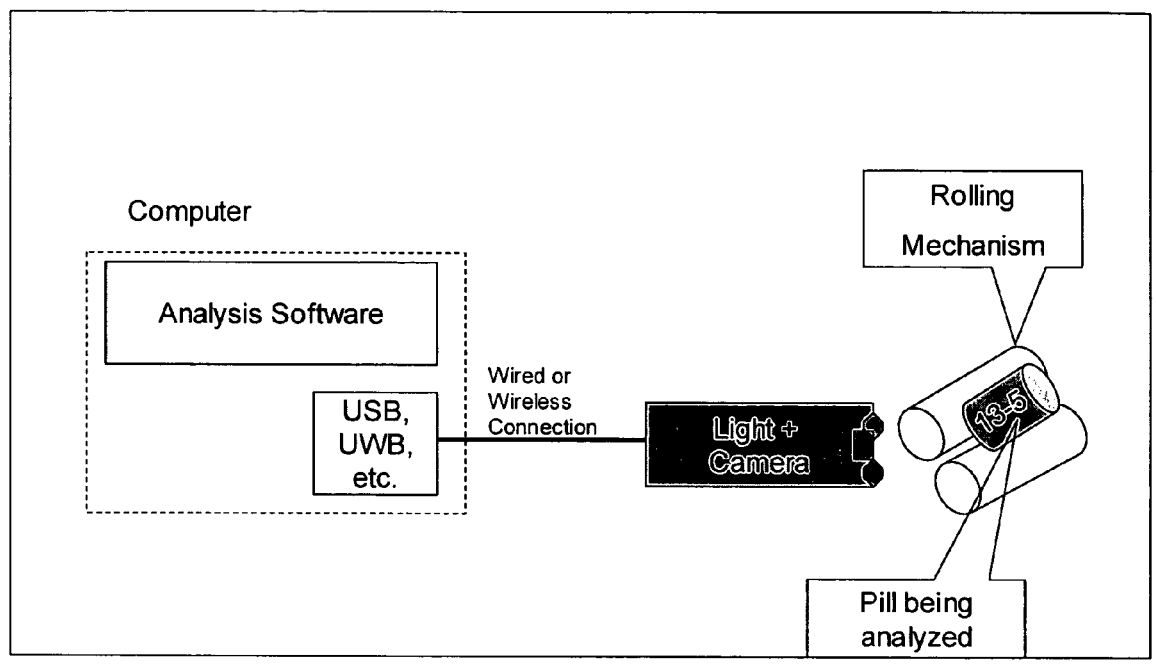
FIG. 2 is a schematic of a pill identification device that is an example of the embodiments of this invention.

FIG. 2 is a schematic of a pill identification device of the embodiments of the invention. The embodiments of the invention relate to a pill identification device comprising a mechanical device that is adapted to roll a pill along various axes of the pill, an optical device (such as a bar code reader, a camera, a scanner or a photodiode) to record or transmit images of the pill, and an algorithm to control the rolling of the pill, to obtain an output of the optical device and/or to compare an identifier of the pill to a database comprising known identifiers of known pills. The pill identification device could further comprise a computer, wherein at least a portion of the algorithm could be in software. The identification device, preferably, the computer, is adapted to report the name of the pill. The pill identification device could further comprise a microchip, wherein at least a portion of the algorithm could be coded. In one embodiment of the invention, at least a portion of the algorithm could be software that resides in a computer and at least another portion of the algorithm could be coded in a microchip.

The mechanical device could include a rolling mechanism comprising rollers as shown in FIG. 2. In other embodiments of the invention, the mechanical device could be a container such as a cup, a bottle or a cone, for example, in which the pill could be placed and rolled along various axes of the pill. For example, when a police officer apprehends a person on a street and finds that the person possesses a pill, the police office could immediately identify the pill by placing the pill in a container, rolling the pill along various axes of the pill while simultaneously scanning the pill using one or more hand-held scanners/cameras. Artificial illumination (LED or light) could be part of the scanner as artificial illumination may be needed to get the image bright enough for the camera. In one embodiment of the invention, the camera could record the images of the pill and then transmit the recorded images to a computer (for example, a computer located at a base station), which contains analysis software to determine the identity of the pill. In yet another embodiment of the invention, the camera might not record the images, but instead could transmit the images directly to the computer. The transmission of the images to the computer could occur over a wired or wireless connection. In yet another embodiment of the invention, the camera and the computer could be a self-contained and independent pill identification device located in the vehicle of the police officer.

In other embodiments of the invention, the pill identification device could further comprise a loader to load the pill into the mechanical device and an ejector to eject the pill out of the mechanical device. In an alternative embodiment of the invention, the mechanical device can sequence through a series of pills. Once a pill has been identified, it can be ejected and a subsequent pill automatically loaded.

The mechanical device could comprise one or more rollers adapted to roll the pill along various axes of the pill. In other embodiments of the invention, the mechanical device could comprise a cup or a cone that is adapted to hold the pill and to roll the pill along various axes of the pill.

Figure 3:
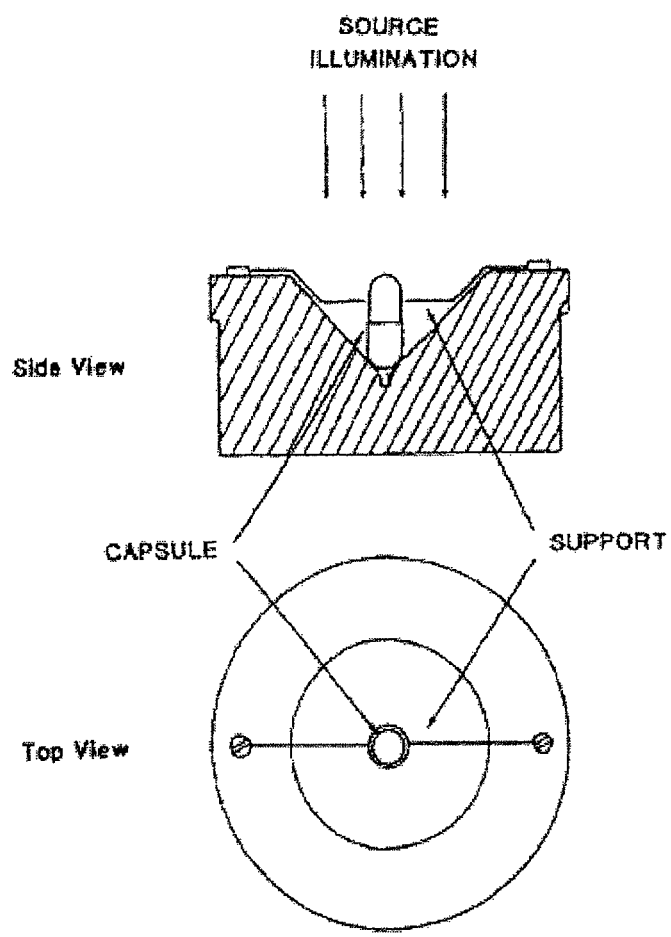
FIG. 3 is a schematic of a mechanical device, which is a container with two separate cones, that is adapted to roll a pill along the axes of the pill.

The pill identification device of embodiments of the invention could further comprise a pill positioning tool adapted to position the pill to a proper position for the optical device to take an image of the identifier of the pill. For example, the container for the pill could be a right circular cone and the pill positioning tool could be a support such as that shown in FIG. 3. This right circular cone has a 90° conical reflector, which when empty, reflects radiation (light beam, laser or any other form of radiation) back toward its source, parallel to the incident beam. When a pill (shown as a capsule in FIG. 3) is positioned along the axis of rotation of the conical reflector with a support as shown in FIG. 3, the light reflected from the surface of the capsule is returned to the source when the incident light is perpendicular to the base of the cone as shown in FIG. 3. Light is then focused at the curved end of the capsule and images of the curved surface of the capsule could be obtained. When the support is removed, the capsule would lie flat along the edge of cone. The capsule could then be rotated within the cone such that images of the cylindrical surface of the capsule could then be obtained.

In yet other embodiments of the invention, the pill identification device could further comprise an infrared or near-infrared analytical tool adapted to detect a composition of the pill, a bar code reader that is adapted to read a bar code placed on the pill, or a light source and a photo-detector to detect the pill and generate a signal to the mechanical device to roll the pill along various axes of the pill. Preferably, the mechanical device is adapted to rotate the pill along each axis of the pill with at least a 360 degrees rotation.

As explained above the turning or rolling of the pill could be done manually by a human. This requires greater effort on the part of the human operating the system, however it may be significantly less expensive.

In one embodiment of the invention, the mechanical device adapted to roll the pill could be a tube at an incline through which the pill would tumble and roll as it proceeds from one end of the tube to the other end. Also, the tube could have protrusions such as those in a clothes washer to promote tumbling and rolling of the pill. The pill could exit the tube and freely fall through air or through some other transparent medium such as water or oil. Furthermore, there could be one or more optical devices recording images of the pill as it traversed through the tube and then fell through air or the transparent medium.

The pill could have a unique identifier on the pill. For example, each drug could be made identifiable by means of a code, such as a bar code, that is registered or imprinted on the medication. The bar code is preferably printed or engraved on the pill. A typical drug pill or tablet has the shape of a sphere, a disk or a cylinder with hemispherical ends. The diameter of such a pill would typically be on the order of 4-10 mm. In the embodiments of the invention, one or more bar code readers or a radial bar code may be used, which provides optimal data images of a small radial surface such as a tablet.

In an alternative embodiment of the invention, a miniaturized version of a conventional bar code, which uses thin parallel bars, may be used as the coding system. The width of bars could be preferably sufficiently small, even less than 0.1 mm, to enable sufficient identification information for the pill to be coded onto the surface of the pill. If the tablet is sufficiently large, a conventional bar code may be attached thereto or a code, preferably a miniaturized conventional bar code, may be applied to the surface of the capsule.

The code, whether a bar code or a radial code, may be applied as bars painted on the pill during or after the manufacturing process. The colors applied to the pill and the colors of the bar code could be made of bio-compatible materials.

The particular code reader for reading the coded pills would vary depending upon the type of code in use. There exist numerous types of coded information readers, each type being applicable to a particular type of code. Most code readers for reading bar codes of the type discussed above are optical code readers. Others types of readers exist for reading other types of codes, such as those for reading magnetically enciphered codes, RF codes, Surface Acoustic Wave codes, magnetic stripe codes, etc.

A typical optical code reader converts the light and dark bars of a bar code into two levels of intensity that are then converted to electrical signals so that they may be recognized and interpreted. These readers typically scan the area where the coded information is registered with a laser beam. The scanning is typically achieved by a moving mirror, such as a reflector that is rotated about a rotational axis. A light source is preferably a laser or laser diode. An optical lens system converts the light into a beam. The beam scans the code and the reflected light passes through an optical lens system that produces an image of the scanned area on an optical device such as a photodetector. The optical lens system reads the very thin and small bar codes on tablets. The reflected light signal is converted by the photoelectric elements into electrical signals in a manner well known in the art. A detection system then determines the width or amplitude or duration or voltage of the electrical signals, which information is used to translate the signals to numbers or characters in a well-known manner.

When a radial bar code is used, the scanning mechanism is preferably of the rotational type, rather than the linear type. When radial bars of two lengths are used, the photoelectric system includes two or more readers, each corresponding in position to the lengths of the bars, to read the light emitted from the bars of different lengths.

If color coded bars or rings are in use, the light source is not a conventional laser beam but is instead a white light source, an incandescent lamp, a halogen lamp, etc. Color interpretation is made by using a series of light filters as is well known in the art.

If the code is engraved on the surface of the pill, the pill could be placed on a transparent surface with a light source positioned such that the light would cast a shadow of the pill on a surface. In the shadow, the engraved code would be seen as protrusions from the main body of the shadow. A reader, such as a bar code reader, scanner, a camera, or photodiode, which is positioned in direct view of the surface on which the shadow is projected, could scan the shadow to detect the protrusions based upon the two light levels of the shadow, and convert these levels to corresponding electrical signals. In one embodiment of the invention, the light source is fixed while a photodetecting element in the reader could scan the image of the shadow. If desired, the shadow may be magnified during detection. Shadow detection may also be used to read codes on the outer peripheral edge of the pill.

For reading an engraved code (which could be a bar code, an indentation in the surface of the pill or a protrusion from the surface of the pill), a light beam could scan the pill surface, preferably in a linear or circular scanning pattern to identify the code. When a scanning light beam hits an edge of an indentation or a protrusion of a code, the change in the height of the surface results in a transient light intensity change that could be detected by the optical device. As the light beam continues to scan an area on the surface of the pill where there is no code, the light beam again has a constant intensity. When the light beam reaches the second edge of an indentation or a protrusion of the code, a second transient in light intensity could be detected by the optical device. The reader can detect the distance or time elapsed between transients as the width of a bar of a bar code, or the distance between the indentation or protrusion.

Other embodiments of the invention relate to a method of detecting a pill, comprising rolling a pill along various axes of the pill, recording images of the pill by an optical device and comparing an identifier of the pill to a database comprising known identifiers of known pills. The method could further comprise positioning the pill to a proper position for the optical device to take an image of the identifier of the pill, loading the pill into a mechanical device, placing the pill in the mechanical device and ejecting the pill out of the mechanical device and reporting the name of the pill.

The pill identification device of the embodiments of the invention could be assembled as shown in FIG. 2 by assembling a pair of rollers, preferably cone-shaped rollers, a scanner, a light source, all as a USB peripheral that transfers the image to a PC, with software on the PC that does the analysis and database comparison. The assembly of the components of the pill identification device could be done such the pill identification device could have different shapes, for example, like a coin dispenser with a slot for the pill to be introduced and having the rollers and other peripheral components connected to the pill identification device. In one variation, there could be a storage chamber within the pill identification device for safe-keeping of the pill. In another variation, there could be an outlet to dispense a pill from the pill identification device.

The advantages of the embodiments of this invention are many. For example, today, a person attempting to identify a pill must manually enter the color and marking information into a database or look at pictures, for example those in the Physician Desk Reference ("PDR") identification pages. The person may not be able to accurately describe the color or shape of the pill. With the embodiments of the invention, the amount of time required to determine the type of unknown pill will be reduced. The error rate for determining the type of unknown pill will also be reduced.

The pill identification device of the embodiments of this invention could be used by hospitals, doctors' offices, field clinics, law enforcement personal, and medical supply vendors among others.

This application discloses several numerical range limitations that support any range within the disclosed numerical ranges even though a precise range limitation is not stated verbatim in the specification because the embodiments of the invention could be practiced throughout the disclosed numerical ranges. Finally, the entire disclosure of the patents and publications referred in this application, if any, are hereby incorporated herein in entirety by reference.

The invention claimed is:

1. A method of detecting a pill, comprising:
    placing the pill flat on a curved wall of a conical container having the shape of a circular cone to allow the pill to rotate within the conical container;
    rotating the pill within the conical container along an axis of rotation of the pill with at least a 360 degree rotation;
    obtaining an image of the pill;
    determining identification data of the pill based on the image of the pill; and
    determining an identifier of the pill based on comparing the identification data of the pill to information related to known pills, the information related to the known pills including identifiers and identification data of the known pills.

2. The method of claim 1, further comprising illuminating the pill for an optical device to capture the image of the pill, the optical device comprising a camera, a photodiode, or a combination thereof.

3. The method of claim 1, further comprising comparing via an algorithm the image of the pill with images of the known pills.

4. The method of claim 3, wherein the algorithm is coded in a microchip.

5. The method of claim 1, further comprising detecting a composition of the pill with an infrared or near-infrared analytical tool.

6. The method of claim 1, further comprising transmitting an emergency signal in response to an emergency response button being activated.

7. The method of claim 1, further comprising reporting the name of the pill.

8. The method of claim 1, wherein the identification data of the pill comprise a bar code, a shape, or a color of the pill.

* * * * *